United States Patent [19]
Haas

[11] Patent Number: 5,788,659
[45] Date of Patent: Aug. 4, 1998

[54] SHOULDER TRACTION DEVICE FOR RELOCATING A DISLOCATED SHOULDER

[76] Inventor: Michael John Haas, 76144 Hwy 1081, Covington, La. 70435-2302

[21] Appl. No.: 766,794

[22] Filed: Dec. 13, 1996

[51] Int. Cl.[6] ........................................ A61F 5/00
[52] U.S. Cl. ........................ 602/36; 602/20; 602/38; 602/4
[58] Field of Search ................ 602/4, 5, 20, 23–24, 602/32, 36–40, 61, 62

[56] References Cited

U.S. PATENT DOCUMENTS

| | | | |
|---|---|---|---|
| 2,515,590 | 7/1950 | Chaffin | 602/36 |
| 2,590,739 | 3/1952 | Wagner et al. | 602/39 |
| 3,618,598 | 11/1971 | Davis | 602/36 X |
| 3,680,552 | 8/1972 | Bell et al. | 602/40 |
| 4,862,878 | 9/1989 | Davison et al. | 602/20 |
| 4,905,713 | 3/1990 | Moranli | 602/20 X |
| 5,383,844 | 1/1995 | Munoz et al. | 602/20 |
| 5,413,552 | 5/1995 | Iwuata | 602/20 X |

*Primary Examiner*—Linda C. Dvorak
*Attorney, Agent, or Firm*—Joseph T. Regard, Ltd. plc

[57] ABSTRACT

A device for relocating dislocated shoulders, providing in-line humeral traction, wherein there is provided an arm isolation component for isolating the elbow area of the arm adjoining the shoulder to which traction is to be applied, the present invention further including a second strap placed about the chest of the patient, under the arm of the afflicted shoulder, for countertraction. The arm isolation component is of a unique design and includes an upper, generally wedge-configured upper isolation component, having a base configured to engage the underside of the upper (humeral) area of arm, the base further including first and second, somewhat aligned, cushion members emanating in generally lateral fashion from opposing sides of the base, the cushion members configured to each engage an opposing side of the upper arm when applied to the base, enveloping that portion of the arm with the application of a first strap which secures the base and cushion members about the arm. The elbow of the user is then flexed to generally about 45°, until it contacts the front face of the wedge member, wherein it is secured via a second strap. Once countertraction has been secured via the chest strap, the physician may apply in-line humeral traction via waist strap anchored to the base of the wedge member near the base of the humerus of the patient, and utilizing one, or a combination of a variety of pre-existing reduction techniques, facilitate relocation of the dislocated shoulder.

11 Claims, 6 Drawing Sheets

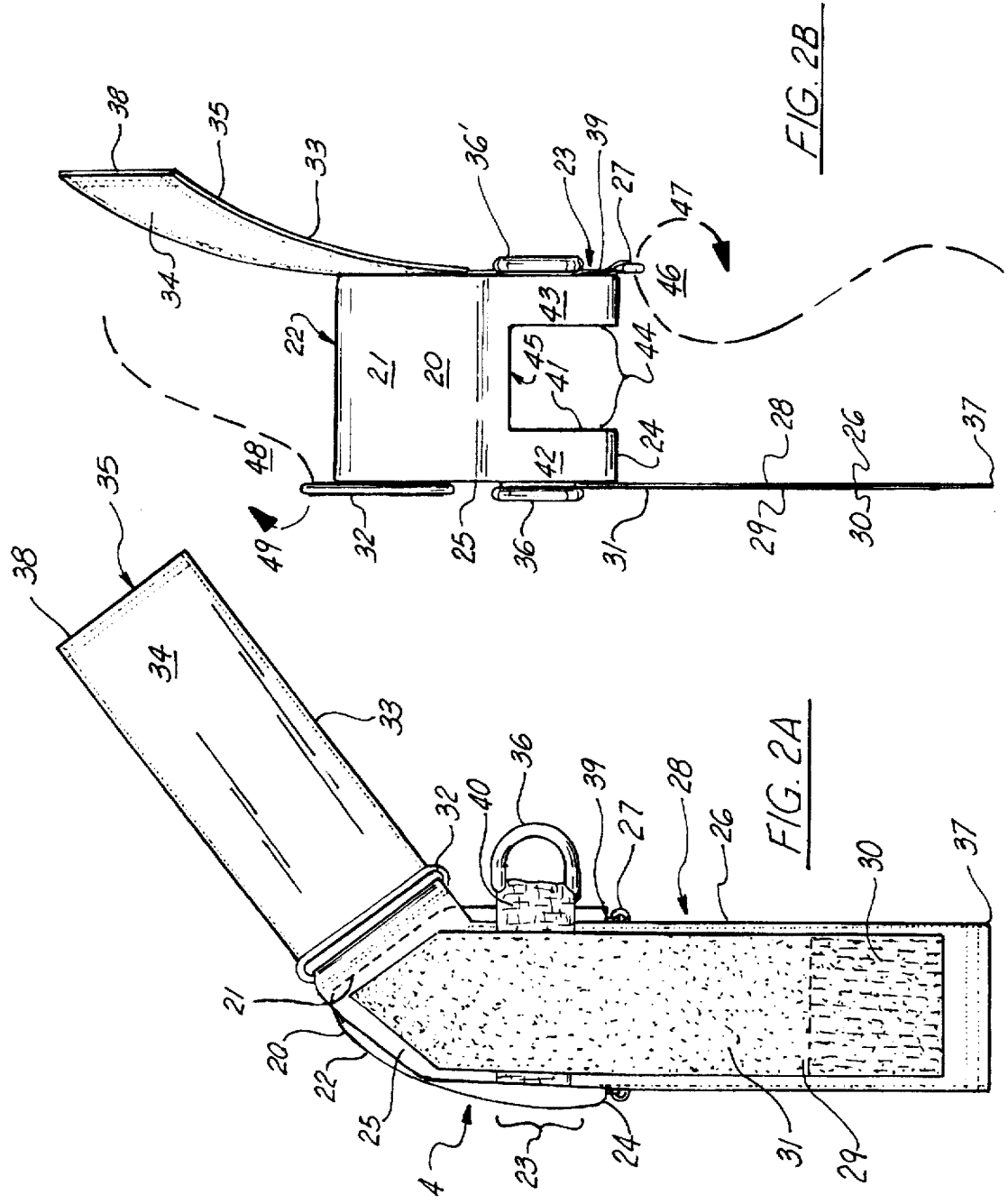

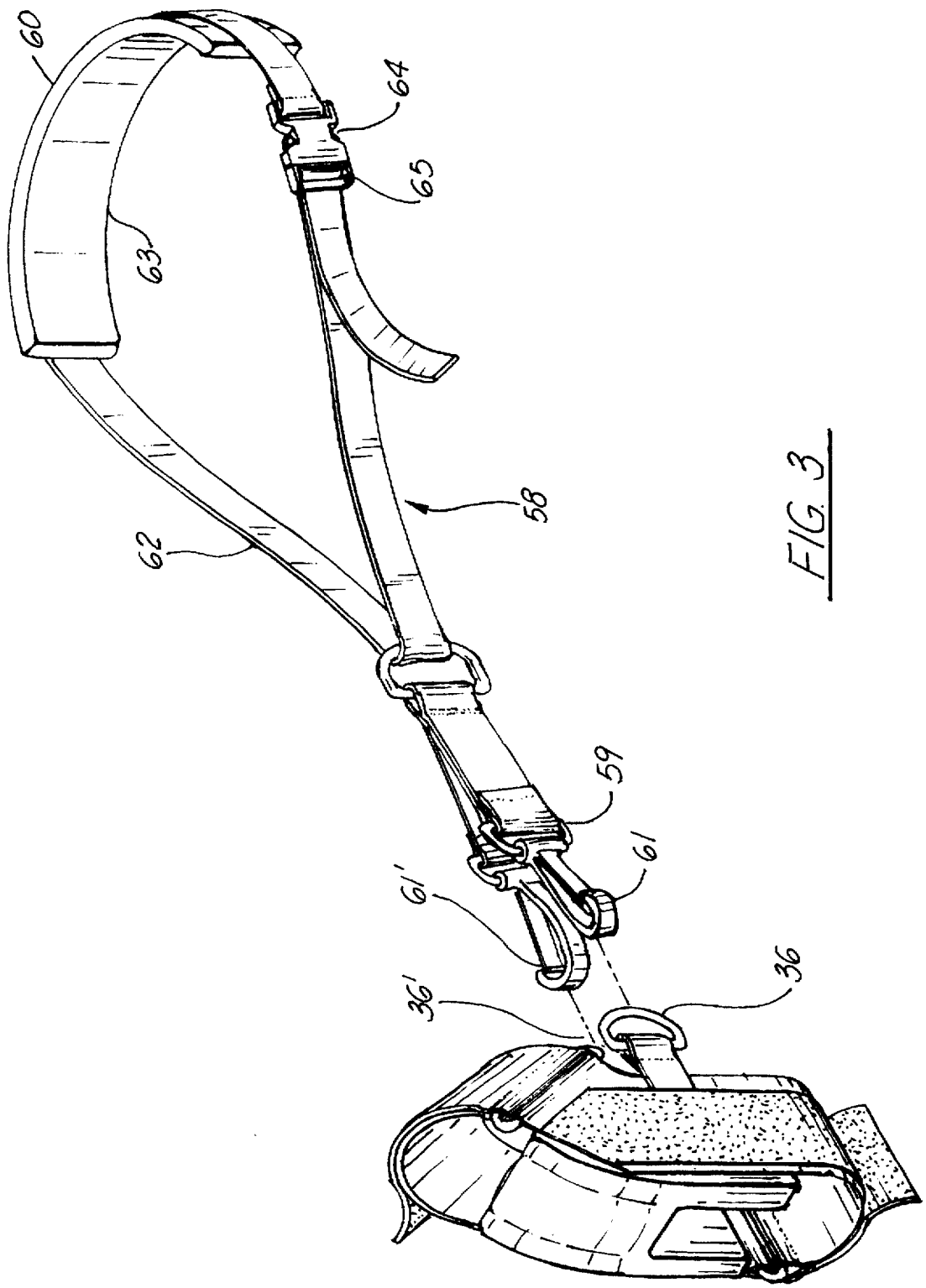

SHOULDER TRACTION DEVICE FOR RELOCATING A DISLOCATED SHOULDER

TECHNICAL FIELD OF THE INVENTION

This invention relates to traction devices, and particularly to a device for relocating dislocated shoulders, providing in-line humeral traction, wherein there is provided an arm isolation component for isolating the elbow area of the arm adjoining the shoulder to which traction is to be applied, allowing the utilization of a waist strap for facilitating traction away from the shoulder and humerus of the patient, the present invention further including a second strap placed about the chest of the patient, under the arm of the afflicted shoulder, for countertraction.

The arm isolation component is of a unique design and includes an upper, generally wedge-configured isolation component, having a base configured to engage the underside of the upper (humeral) area of arm, the base further including first and second, somewhat aligned, cushion members emanating in generally lateral fashion from opposing sides of the base, the cushion members configured to each engage an opposing side of the upper arm when applied to the base, enveloping that portion of the arm with the application of a first strap which secures the base and cushion members about the arm. The elbow of the user is then flexed to generally about 45°, until it contacts the front face of generally wedge configured, upper isolation component, wherein it is secured via a second strap.

Once countertraction has been secured via the chest strap, the physician may apply in-line humeral traction via waist strap anchored to the base of the upper isolation component member near the base of the humerus of the patient, and utilizing one, or a combination of a variety of pre-existing reduction techniques, facilitate relocation of the dislocated shoulder.

BACKGROUND OF THE INVENTION

Reduction techniques for treating shoulder dislocation go back at least to the Egyptians, having been depicted in hieroglyphics, with one of the most effective techniques being attributed to Hippocrates.

Nonetheless, there has yet to be provided a device for facilitating effective, comfortable, in-line humeral traction for reduction of anterior shoulder dislocation.

In the United States, it has been indicated that approximately 48 people per 100,000, between the ages of 15 and 60 suffer shoulder dislocations in a given year. Dislocation of the glenohumeral joint has been cited as the most common major joint dislocation in the body, with anterior dislocations occurring 98% of the time.

Present methods of treatment include four areas: traction methods, leverage methods, scapular manipulation, and combinations thereof. The modified Hippocratic technique, discussed herein, represents a vast improvement over earlier methods, but there has not been provided to date satisfactory equipment for practicing same.

A listing of patents and non-patent publications which may be of pertinence to the present invention follow:

| Patent Number | Inventor | Issue Date |
|---|---|---|
| 5451203 | Lamb | 09/19/1995 |
| 4844056 | Peters | 07/04/1989 |

-continued

| Patent Number | Inventor | Issue Date |
|---|---|---|
| 4573482 | Williams, Jr. | 03/04/1986 |
| 4232664 | Blatt | 11/11/1980 |
| 3698389 | Guedel | 10/17/1972 |
| 3888244 | Lebold | 06/10/1975 |

U.S. Pat. No. 4,844,056 teaches a "Traction Device and Method for Relocating Dislocated Shoulders", which teaches a bent rigid member device for isolating the elbow area of the patient for applying traction in the anterior reduction of dislocated shoulders, including a second countertraction strap about the chest of the patient.

This patent is perhaps the most pertinent reference known to the inventor, as the technique incorporates elements of the modified Hippocratic technique, like the applied for invention, but the "rigid" device for isolating the elbow area of the patient is fully distinguishable in form and function.

U.S. Pat. No. 5,451,203 teaches a "Traction Mechanism" utilizing a tube of flexible material having an inner chamber which envelopes an anatomical appendage, which can be used to apply traction on same.

U.S. Pat. No. 3,888,244 teaches an isolation system for the elbow area of a patient, comprising a bendable semirigid member.

U.S. Pat. No. 3,698,389 teaches an "Elbow Locking Device" comprising a hinged rigid shell, isolating the elbow of the patient.

U.S. Pat. No. 4,573,482 teaches a sleeve mounted about a patient's appendage, combined with a strap which is affixed to a treating physician for applying traction via said sleeve to said patient's appendage.

U.S. Pat. No. 4,232,664 teaches an arm sling, which envelopes the elbow area of the user, and is secured by hook and loop straps, which sling is indicated as being fabricated of a foam material.

Non-Patent Publications of some pertinence include:

Riebel MD, Gregory D., McCabe MD, John B.; "Anterior Shoulder Dislocation: A Review of Reduction Techniques", *The American Journal of Emergency Medicine;* 9(2) (March 1991); 180–188. This article discusses several techniques for relocation of a dislocated shoulder, including the Hippocratic technique, which is indicated as effective but potentially injurious.

Bahn, S., Mehara, A. K.; "A Simple and Universal Method for Reduction of Dislocation of the Shoulder"; *International Orthopaedics* 18 (1994); 14–15. A method of shoulder dislocation reduction having the patient on their contral lateral side and lifting up.

Norling MD, Ph.D, Rolf; "Intra articular Pathology in Acute, First-Time Anterior Shoulder Dislocation: An Arthroscopic Study"; *The Journal of Arthroscopic and Related Surgery* 9(5) (1993); 546–549. Article on Arthroscopic procedures to evaluate shoulder stability in patients with anterior shoulder dislocations.

Westin MD, Craig D., Gill MD, Edward A., Noyes MD, Michael E, and Hubbard MD, Margaret; "Anterior Shoulder Dislocation: A Simple and Rapid Method for Reduction", *The American Journal of Sports Medicine;* 23 (3) (1995): 369–71; This article analyzes a shoulder relocation technique wherein the patient sits in a chair, and a stocking is wrapped about the proximal forearm in order to apply traction to the patient.

Titentilli, ed., *Emergency medicine: A Comprehensive Study Guide* 4th Edition (1996) 1239–1240. This reference, particularly FIG. 226-6 and accompanying discussion on page 1240, discusses the Modified Hippocratic Technique, wherein the patient is in the supine position, and countertraction is employed, much like the technique implemented in the present invention:

"The patient is supine with the arm abducted and elbow flexed at ninety degrees. A sheet is tied and placed across the thorax of the patient then around the waist of the assistant. Another sheet is tied and placed around the forearm of the patient at the elbow and the waist of the physician. The physician gradually applies traction as the assistant provides countertraction. Gentle internal and external rotation or outward pressure on the proximal humerus may aid reduction."

This technique is an improvement over the original reduction technique advocated by Hippocrates, which involved placing the physician's foot into the axilla of the patient, and effecting longitudinal traction on the arm by the physician leaning backwards, and sometimes severely injuring the patient, the "cure" causing more harm than the injury.

Nonetheless, it is surprising that textbook medical techniques still teaches that physicians must tie themselves up in sheets to accomplish relocation of a dislocated shoulder. The prior art has thereby yet to provide a relatively comfortable, safe, and secure means to facilitate reduction of an anteriorly dislocated humerus—the dislocated shoulder.

GENERAL, SUMMARY DISCUSSION OF THE INVENTION

Unlike the prior art, the present invention provides a structured, better controlled, more efficient and effective system for facilitating relocation of a dislocated shoulder, with a system which would take less time to set up and utilize than earlier prior art systems, while requiring less physical effort on the part of the physician in facilitating the reduction of the shoulder dislocation.

The present invention is designed to facilitate less traumatic and more efficient reduction of an anteriorly dislocated shoulder, allowing the attending physician to apply traction, leverage, scapular manipulation, and combinations of same, as taught in, for example, the modified Hippocratic technique.

The invention contemplates an arm isolation component, wherein the preferred embodiment of the invention is formed of non-rigid material configured to engage and isolate the elbow of the user at generally about a 45° angle, the actual degree of which can vary widely depending upon the patient, physician, and injury.

As indicated, the arm isolation component includes an upper, generally wedge-configured isolation component, having a base configured to engage the underside of the upper (humeral) area of arm, the base further including first and second, somewhat aligned, cushion members emanating in generally lateral fashion from opposing sides of the base, the cushion members configured to each engage an opposing side of the upper arm when applied to the base, enveloping that portion of the arm with the application of a first strap which secures the base and cushion members about the arm. The elbow of the user is then flexed to generally about 450°, until it contacts the front face of the upper isolation component, wherein it is secured via a second strap.

The arm isolation component is configured to engage a traction strap to be placed about the treating physician, situated on the component in the vicinity of the elbow of the patient, so as to allow vector force to be applied as traction away from the humerus and afflicted shoulder.

Once countertraction has been secured via the chest strap, the physician may apply in-line humeral traction via waist strap anchored to the base of the upper isolation component near the base of the humerus of the patient, and utilizing one, or a combination of a variety of pre-existing reduction techniques, facilitate relocation of the dislocated shoulder.

It is therefore an object of the present invention to provide a system for relocating a dislocated shoulder which allows the user to provide in-line humeral traction to facilitate a more efficient and effective reduction procedure.

It is another object of the present invention to provide a system for facilitating relocation of a dislocated shoulder, wherein there is provided an arm isolation component configured to comfortably position and isolate the arm of the patient in a manner as to allow the application of traction force by the physician in an efficient, effective manner.

It is another object of the present invention to provide a traction system which may be utilized with patients of varying sizes, with like positive results.

It is another object of the present system to provide a device which may be utilized to practice the modified Hippocratic technique without the need for tying bed sheets or the like.

Lastly, it is an object of the present invention to provide a shoulder relocation device which is easy and fast to implement, effective in operation, and requires little in the way of maintenance or service.

BRIEF DESCRIPTION OF DRAWINGS

For a further understanding of the nature and objects of the present invention, reference should be made to the following detailed description, taken in conjunction with the accompanying drawings, in which like parts are given like reference numerals, and wherein:

FIG. 2A is a side view of the arm isolation component of the invention of FIG. 1, illustrating the first and second isolation straps and their relation to the main body component.

FIG. 2B is an end view of the arm isolation component of the invention of FIG. 2A, illustrating the cushion members emanating in generally lateral fashion from opposing sides of the base, the upper isolation area, and their relation to the base and main isolation areas.

FIG. 3 is an isometric view of the shoulder traction device of FIG. 1, illustrating the installation of the traction belt to the arm isolation component.

DETAILED DISCUSSION OF THE INVENTION

Figure 1:
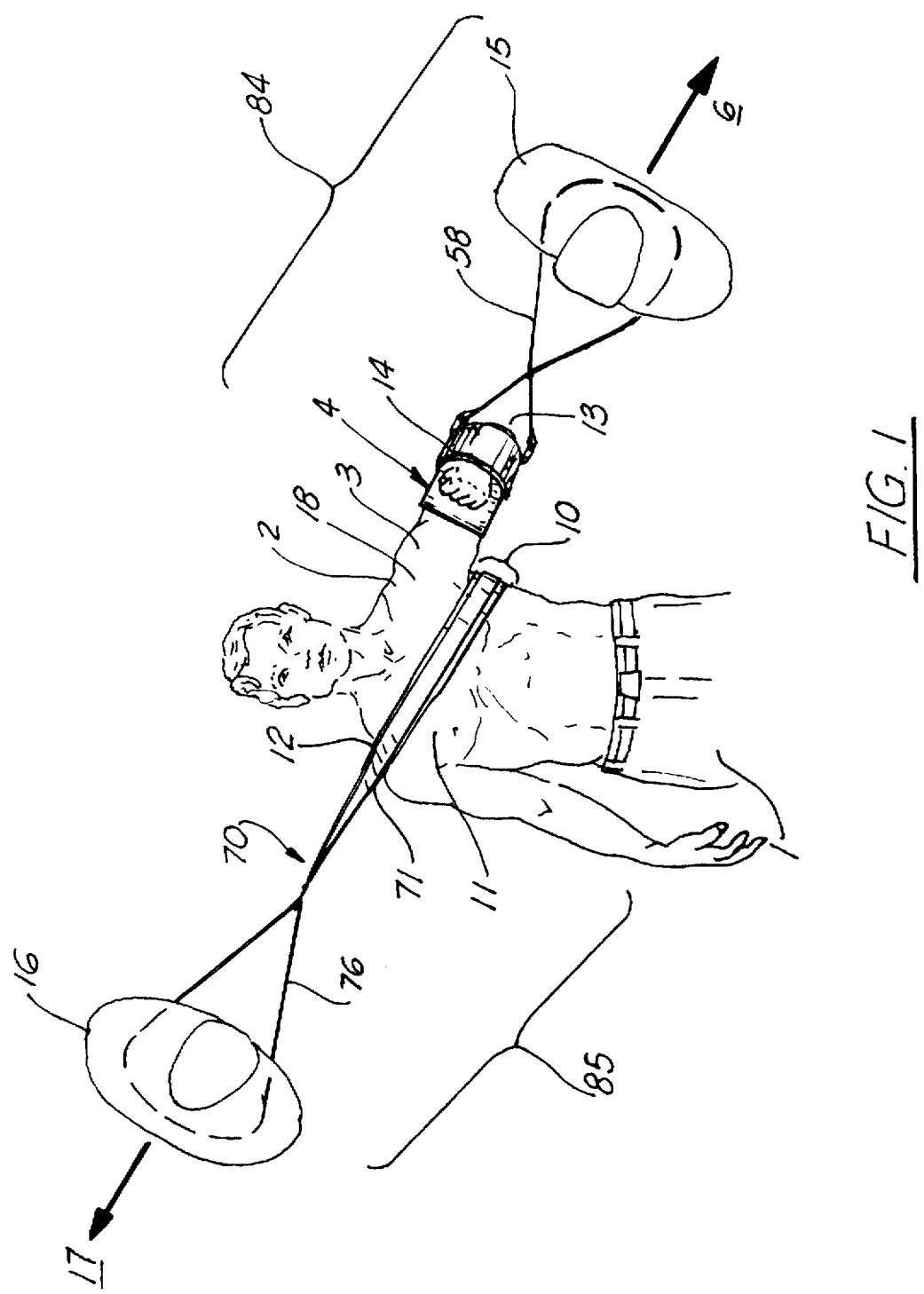
FIG. 1 is a top view of the system of the present invention, illustrating the shoulder traction device of the present invention being utilized with a patient, shown in a supine position, further illustrating the traction and counter traction components, and the vector forces associated with each when practicing a modified version of the Hippocratic technique.

Referring to FIG. 1 of the drawings, the preferred embodiment of the shoulder traction device of the present invention is shown in applying traction to a patient 1 having a dislocated shoulder 2, providing a traction 84 and countertraction 85 components for reduction and relocation.

The exemplary technique being illustrated for purposes of conveying the device of the present invention is a variation of the modified Hippocratic technique, wherein the patient is in the supine position during the reduction, with his arm extending outwards, elbow down, such that the humerus is at an angle of generally about 45 degrees relative to the patient's spine, and the spine and humerus of the patent are situated on about the same plane. It is noted that other reduction techniques already known and practiced in the art may be utilized, and that the device of the present invention is not limited to the technique illustrated herein. These exemplary angles are but averages, and can vary substantially depending upon the circumstances of each case.

The traction components of the present invention include an arm isolation component 4 applied to the arm 3 associated with the dislocated shoulder 2 of the patient, the isolation component configured to isolate the upper arm and forearm 14 at a relative angle at generally not more the 90 degrees, and generally on the order of about 45 degrees by placing the arm about the component and engaging same with straps.

A traction belt 58 communicates with the arm isolation component 4 in the vicinity of the elbow 3 of the patient, which traction belt is generally placed about the waist of the attending physician 15, so that he may provide gradual, controlled traction force in general linear alignment with the humerus 18 of the patient, and away 6 from the shoulder of the patient, while, as desired, manipulating the arm, to relocate the dislocated shoulder.

The countertraction component 85 is provided by a countertraction belt 70, which includes a chest loop 71 having first and second ends, the first end situated about the underarm 10 below the afflicted shoulder, across the chest 11 of the patient, and generally over about the unafflicted shoulder 12, the second end of the chest loop communicating with an attendant waist belt 76, situated about the waist of an attendant 16.

The traction and countertraction components are configured to provide opposing, linearly aligned traction 6 and countertraction 17 vector forces in general alignment with the humerus 3 of the patient, providing the most efficient and effective use of force for anterior reduction and relocation of the glenohumeral joint.

Referring to FIGS. 2A–2B, the preferred embodiment of the arm isolation component 4 of the present invention is fabricated of a non-rigid, relatively pliable material, such as, for example, vinyl-coated medium-high density PVC foam, forming an upper isolation component 20 and a base 23 having a bottom 24, the upper isolation component having a front 21 face (shown in phantom in FIG. 2A), situated at an angle of generally about 45 degrees relative to the base, forming a sloped surface. A rear face 22 is also provided, and is shown also a 45 degree slope, but this angle can vary considerably as it is not critical to the function of the system.

Situated on the first side 25 of the arm isolation component 4 is a humerus strap 26 shown extending beyond the base 23 and bottom 24 of component 4, and having a width generally corresponding to the first side 25 of the component, the humerus strap having inner 28 and outer 29 faces, the outer face having situated thereon hook and loop fasteners, the hook fasteners 30 situated in an area associated with the distal end 37 of the strap 26, the loop fasteners 31 situated on the strap in the area not occupied by the hook fasteners, although the fasteners could be situated visa-versa. Also, alternative fastening means could be used, such as, for example, releasable adhesive strips, friction loops, and the like.

Continuing primarily with FIGS. 2B, while referring to FIG. 2A, the humerus strap 26 is configured to engage strap loop 27 situated at the bottom 24 of the base 23, adjacent to the second side 39 of the component, the strap passing through (46 in FIG. 2B), and be looped around (47 in FIG. 2B) so that the hook fasteners 30 can engage the loop fasteners 31.

An isolation strap 34 is shown emanating from the second side 39 of the component 4, the strap projecting in lateral fashion relative to the slope of front face 21, and is of a length to pass over the front face, with room for the placement of the patients's forearm thereunder, with the end 38 of the strap to pass through 48 a strap loop 32 situated generally adjacent to the opposing side edge. Like the humerus strap 26, the isolation strap 34 has inner 34 and outer 35 faces, the outer face having a hook and loop fastening means, with, for example, the hook fastener generally near the end 38 of the strap, on the outer face 35 thereof, the loop on the same face, but generally nearer the upper isolation component 20. The strap is passed through 48 the strap loop 32, as indicated, and looped around 49, such that the strap may be tightened, and the hook fastener may be brought to engage the loop fastener, engaging same.

Figure 2C:
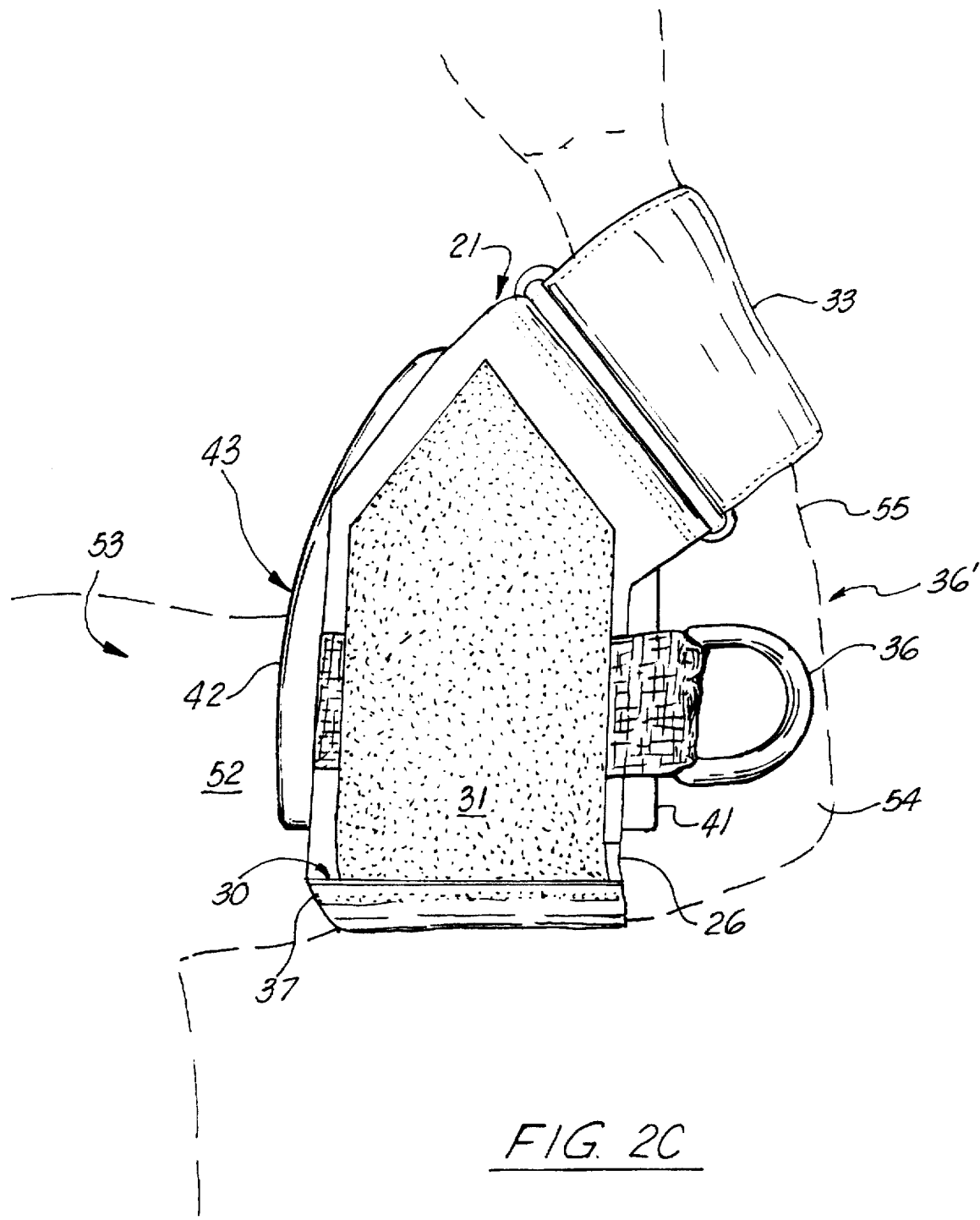
FIG. 2C is a side view of the implemented arm isolation component of FIG. 2A, illustrating in phantom the patient, and the installation and placements of the first and second isolation straps relative therethrough.

As shown by the end view of FIG. 2B, and also referring to FIG. 2C, the base 23 of the component includes first 42 and second 43, somewhat parallel aligned, cushion members having a front 41 area, each of said cushion members 42, 43 emanating in generally lateral fashion from opposing lower sides of the base, the cushion members 42, 43 configured to each engage an opposing side of the upper arm of the patient when applied in a space formed therebetween 44, the patient's arm, engaging the underside 45 of the base, enveloping that portion of the arm with the application of humerus strap 26 and end, through 46 the strap loop 27, and looped 47 back, tightened, and brought into face-to-face contact with itself, so that the hook fastener 30 engages the loop fastener 31, securing the base and cushion members 42, 43 about the arm, and thereby isolating the arm, as shown in FIG. 2C.

As shown, the elbow region 54 of the arm 53, is thereby positioned against the front face 21, with the forearm angled at less than 90 degrees relative to the upper arm, and ideally isolated at an angle of about 45 degrees, with the isolation strap 33 isolating the forearm area 55, and the humerus area 52 isolated by the humerus strap 26, which is shown with the end 37 looped back, and the hook fastener 30 on the outer face of the strap thereby engaging the loop fastener 31 in face to face engagement, allowing the user to tighten the strap to the desired amount, and secure same easily, securely, and quickly.

Referring to both FIGS. 2B and 2C, first 36 and second 36' strap rings are provided emanating from the front 41 of first 42 and second 43 cushion members, respectively, and are configured to engage the traction belt 58, as shown in FIG. 3.

Continuing with FIG. 3, the traction belt 58 has first 59 and second 60 ends, the first end having situated thereon belt clips 61, 61', configured to engage strap rings 36, 36', respectively, the second 60 end having a waist belt 62 configured to fit about the waist of the attending care giver, the waist belt having a cushion 63, a buckle 64, as desired, and an adjustment loop 65.

Figure 4:
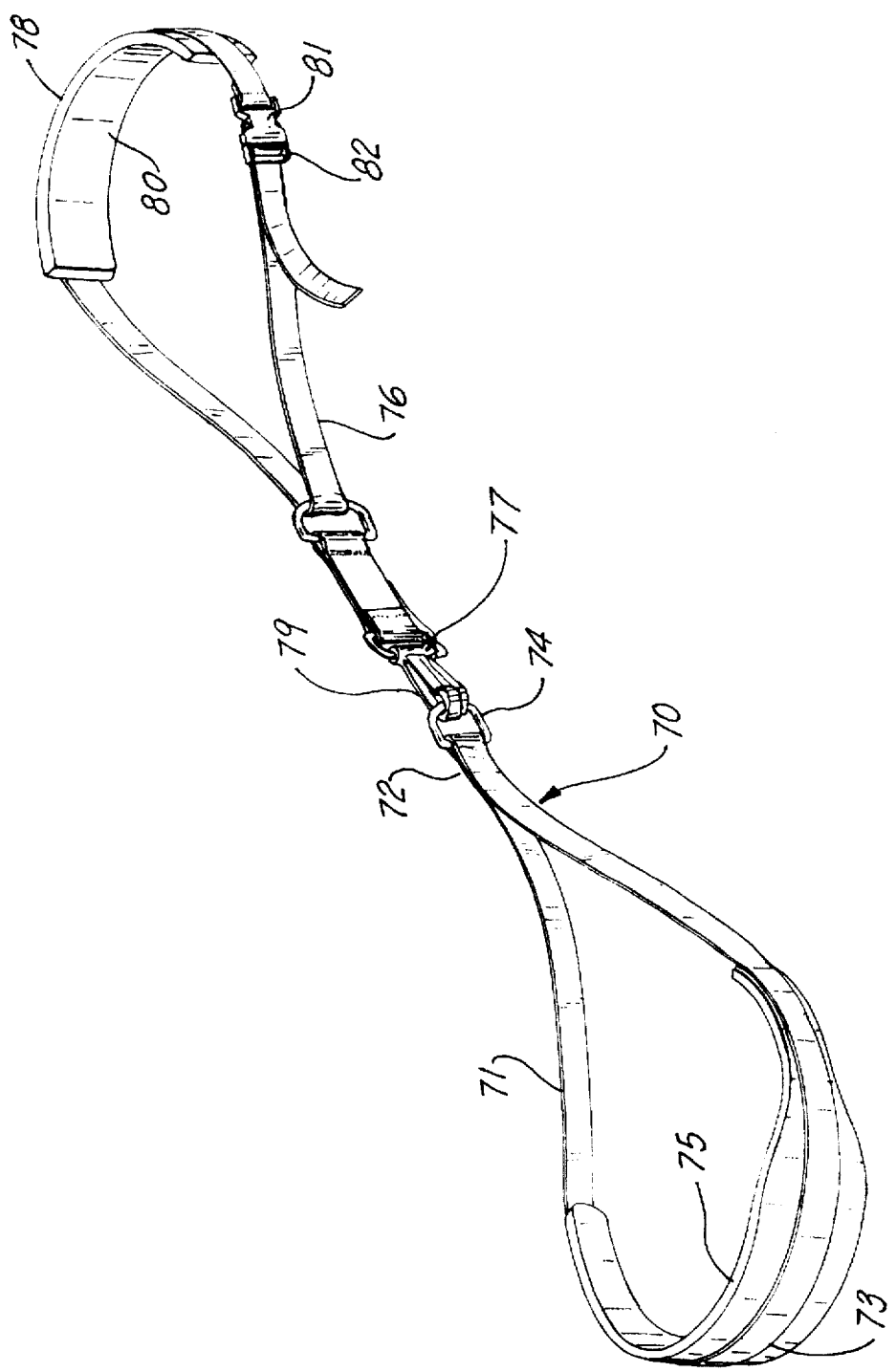
FIG. 4 is an isometric view of the shoulder traction device of FIG. 1 illustrating the countertraction belts of the patient and assistant.

FIG. 4 sets forth the countertraction belt 70 of the present invention, wherein there is provided a chest loop 71 having a first 72 and second 73 end, the first 72 having a cushion 75 situated thereon, the second 73 end having a ring 74 situated thereon, the cushion and second end 73 configured to fit under the arm of the dislocated shoulder of the patient, the first 72 end configured to lie generally outside of the unafflicted shoulder of the patient.

The ring 74 of the chest loop 71 is configured to engage an attendant waist belt 76 or the like, the attendant waist belt having a first 77 and second 78 end, the first end having a clip 79 for removably engaging the ring 74, the second 78 end having a cushion 80 to generally engage the lower back and/or hip of the assistant when in use, the belt further including a buckle 81 and adjustment loop 82.

Figure 5:
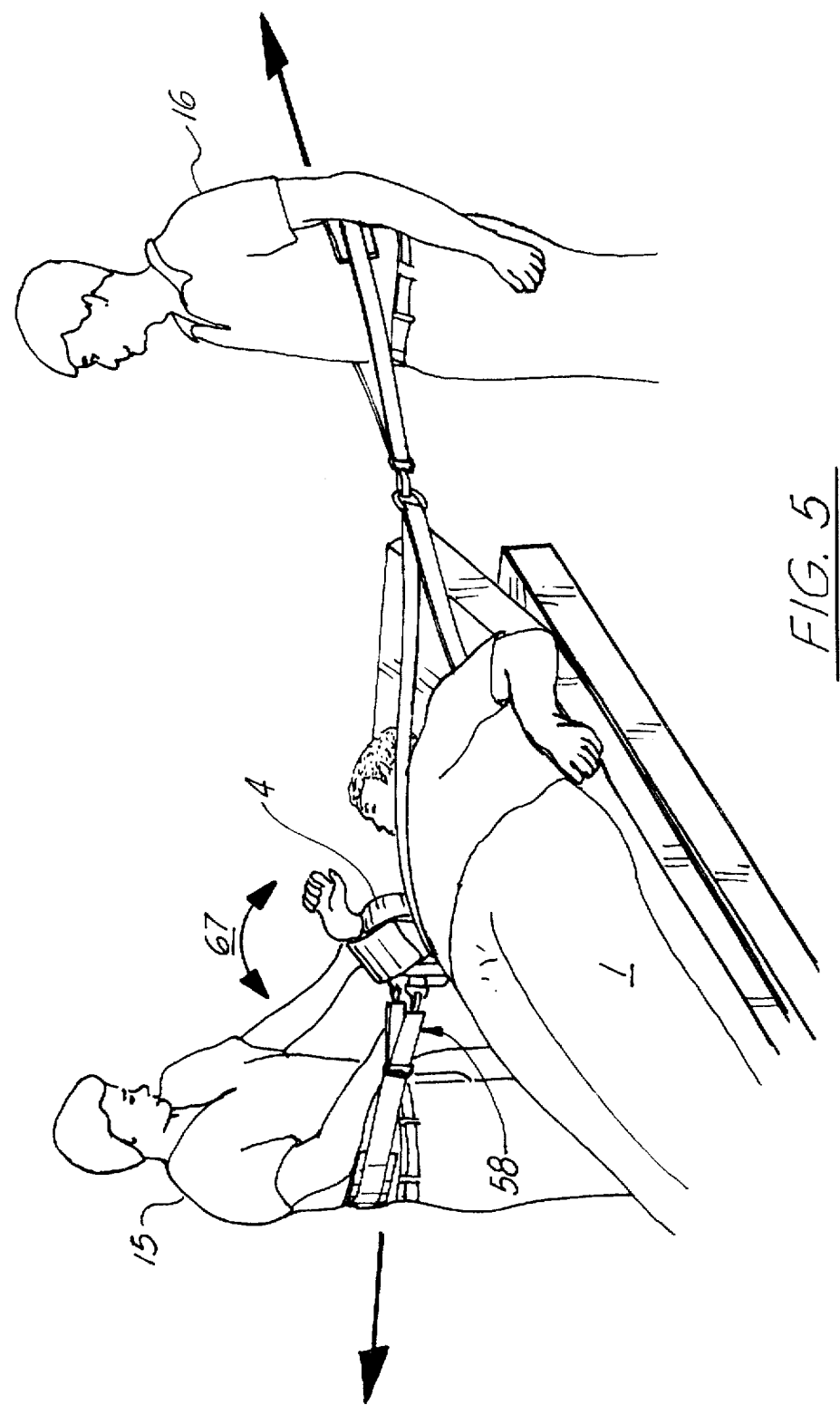
FIG. 5 is an isometric view of the invention of FIG. 1, further illustrating the implementation of the device of the present invention in practicing a modified version of the Hippocratic technique.

Referring to FIG. 5 and the earlier referenced FIG. 1, in use, the patient 1 is placed in a dorsal supine position. Intravenous access lines may be placed into the opposite extremity, as necessary. The countertraction belt is placed about the patient's chest, with the second end and cushion placed under the axilla of the affected arm, and the first end placed across the unaffected shoulder, enveloping the patient's chest and unaffected shoulder with the strapping. The assistant 16, having the waist belt loosely thereabout his waist, engages the clip to the ring situated at the first end of the countertraction belt.

Next, any jewelry or the like is removed from the patient's afflicted arm, and the arm isolation component 4 is installed as earlier discussed, with the forearm flexed and isolated thereabout, and the traction belt 58 placed about the waist of the attending physician, and clipped to the arm isolation component.

The physician may then position the arm with the forearm in a generally lateral position relative to the patient, and the upper arm and humerus at about a forty-five degree angle relative to the spine of the patient, and facing the patient, begin applying gradual traction by leaning backwards, with the assistant providing opposite and counter force, as countertraction.

The physician may then provide reduction or relocation utilizing the method which he desires, which could include, with the application of traction, adjusting 67 the forearm to position the proximal humerus to aid in reduction.

It is noted that the present invention may utilize other configurations of traction and countertraction belts and straps, and other techniques of reduction. For example, traction may be supplied by a weight, and countertraction may be supplied by an anchoring strap affixed to furniture or another anchoring object.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A traction system for relocating a dislocated shoulder on a patient said device interfacing the arm associated with the dislocated shoulder, the arm having an underside, an upper arm area having a humerus therein, an elbow area, a forearm, an underarm, the patient further having a chest and unafflicted shoulder area, said traction system comprising:

a traction component, comprising:

an arm isolation component fabricated of non-rigid, relatively pliable material, said arm isolation component having first and second side walls, a base, and a front, said arm isolation component comprising an upper isolation component, forming the upper portion of said arm isolation component, said base having a front, a bottom, and first and second sides, said base forming the lower portion of said arm isolation component;

said upper isolation component further comprising a front face having a sloped surface;

said base further comprising first and second, aligned, cushion members having a front area, each of said cushion members emanating in generally lateral fashion from opposing lower sides of said base, said cushion members forming therebetween an upper arm engagement area, for engaging and generally enveloping the underside of the patient's upper arm;

humerus strap means associated with said cushion members for strapping said first and second cushion members about said patent's upper arm, such that said bottom of said base rests in contact with the underside of the patient's upper arm;

forearm strap means associated with said front face of said upper isolation component, for strapping said the underside of the patient's forearm to said front face of said upper isolation component, such that the patient's forearm contacts said sloped surface of said front face;

a traction belt associated with said arm isolation component for applying traction force generally aligned with the humerus of the patient, said traction force directed generally away from the patient;

separate counter-traction means for providing opposing counter-traction force to said traction force.

2. The traction system of claim 1, wherein said counter-traction means comprises a countertraction belt, said countertraction belt further comprising:

a chest belt having first and second ends, said first end having a cushion, said second end having an engagement ring;

an attendant waist belt having first and second ends, said first end having a cushion, said second end having a clip configured to engage said engagement ring, said waist belt further comprising adjustment means for adjusting the size of said waist belt to fit the user.

3. The traction system of claim 2, wherein said arm isolation component further comprises first and second connectors situated adjacent to said first and second cushion members, respectively, and said traction belt further comprises first and second ends, said second end further comprising engagement means for engaging said first and second connectors.

4. The traction system of claim 3, wherein said first and second connectors comprise first and second strap rings, and wherein said engagement means further comprises first and second clips configured to engage said first and second strap rings, respectively.

5. A traction system, comprising:

an arm isolation component, said arm isolation component having first and second side walls, a base, and a front, a bottom, and first and second sides, said base forming the lower portion of said arm isolation component;

said arm isolation component further comprising a front face having a sloped surface;

said base having further comprising first and second, aligned, cushion members having a front area, each of said cushion members emanating in generally lateral fashion from opposing lower sides of said base, said cushion members forming therebetween an upper arm engagement area;

humerus strap means associated with said cushion member for strapping said first and second cushion members;

forearm strap means associated with said front face of said arm isolation component, for strapping said front face of said arm isolation component;

a traction belt associated with said arm isolation component for applying traction force to said arm isolation component.

6. The traction system of claim 5, wherein there is further provided a separate counter-traction means for countering said traction force, said counter-traction means comprising a countertraction belt, said countertraction belt further comprising:

a chest belt having first and second ends, said first end having a cushion, said second end having an engagement ring;

an attendant waist belt having first and second ends, said first end having a cushion, said second end having a clip configured to engage said engagement ring, said waist belt further comprising adjustment means for adjusting the size of said waist belt to fit the user.

7. The traction system of claim 6, wherein said arm isolation component further comprises first and second connectors situated adjacent to said first and second cushion members, respectively, and said traction belt further comprises first and second ends, said second end further comprising engagement means for engaging said first and second connectors.

8. The traction system of claim 7, wherein said first and second connectors comprise first and second strap rings, and wherein said engagement means further comprises first and second clips configured to engage said first and second strap rings, respectively.

9. The traction system of claim 8, wherein said arm isolation component is formed of vinyl coated, PVC foam.

10. The method of relocating a dislocated shoulder on a patient utilizing a device which interfaces the arm associated with the dislocated shoulder, the arm having an underside, an upper arm area having a humerus therein, an elbow area, a forearm, an underarm, the patient further having a chest and unafflicted shoulder area, said method comprising the steps of:

a) providing a traction component, comprising:

an arm isolation component, said arm isolation component having first and second side walls, a base, and a front, a bottom, and first and second sides, said base forming the lower portion of said arm isolation component;

said arm isolation component further comprising a front face having a sloped surface;

said base having further comprising first and second, aligned, cushion members having a front area, each of said cushion members emanating in generally lateral fashion from opposing lower sides of said base, said cushion members forming therebetween an upper arm engagement area;

humerus strap means associated with said cushion member for strapping said first and second cushion members;

forearm strap means associated with said front face of said arm isolation component, for strapping said front face of said arm isolation component;

a traction belt associated with said front area of said first and second cushion members of said arm isolation component for applying traction force generally aligned with said arm isolation component;

b.) placing said patient in a dorsal supine position, the arm of the patient extending outwards, elbow down, such that the humerus is at an angle not to exceed ninety degrees relative to the patient's spine, the spine and the humerus of the patient situated about on the same plane;

c.) placing said base of said arm isolation component upon the upper arm area of the patient, such that said first and second cushion members partially envelope said upper arm area, and said upper arm engagement area formed by said cushion members engages the underside of the patient's arm, with the front of said arm isolation component facing towards the patient's elbow;

d) strapping said upper arm of the patient to said base of said arm isolation component via said strapping means;

e) flexing the patient's arm, conveying the forearm of the patient against said sloped surface of said front face of said arm isolation component;

f.) strapping said forearm of the patient to said sloped surface of said front face of said arm isolation component;

g.) affixing said traction belt to said arm isolation component, and aligning said traction belt with the humerus of the patient to provide traction force along a vector generally aligned with said humerus of the patient;

h.) providing traction force via said traction belt.

11. The method of claim 10, wherein there is further provided, after step "g", of affixing a counter-traction belt to the patient, said counter traction belt aligned to provide countertraction force along a vector generally aligned with said humerus of the patient.

* * * * *